US010896538B2

(12) United States Patent
Mory et al.

(10) Patent No.: US 10,896,538 B2
(45) Date of Patent: Jan. 19, 2021

(54) SYSTEMS AND METHODS FOR SIMULATED LIGHT SOURCE POSITIONING IN RENDERED IMAGES

(71) Applicant: KONINKLIJKE PHILIPS N.V., Eindhoven (NL)

(72) Inventors: Benoit Jean-Dominique Bertrand Maurice Mory, Mercer Island, WA (US); Emmanuel Mocé Serge Attia, Paris (FR); Jean-Michel Rouet, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/347,739

(22) PCT Filed: Oct. 27, 2017

(86) PCT No.: PCT/EP2017/077535
§ 371 (c)(1),
(2) Date: May 6, 2019

(87) PCT Pub. No.: WO2018/083011
PCT Pub. Date: May 11, 2018

(65) Prior Publication Data
US 2019/0318534 A1    Oct. 17, 2019

(30) Foreign Application Priority Data

Nov. 7, 2016    (EP) ..................................... 16306455

(51) Int. Cl.
*G06T 15/80*    (2011.01)
*G16H 30/40*    (2018.01)
(Continued)

(52) U.S. Cl.
CPC ............ *G06T 15/80* (2013.01); *G06F 3/0488* (2013.01); *G06T 15/08* (2013.01); *G16H 30/40* (2018.01); *G06T 2207/10132* (2013.01)

(58) Field of Classification Search
None
See application file for complete search history.

(56) References Cited

U.S. PATENT DOCUMENTS 8,633,913 B1 *  1/2014  Raghu ................. G08G 5/0021
                                                340/945
2003/0231789 A1 * 12/2003 Willis ................. A61B 5/0073
                                                382/128

(Continued)

FOREIGN PATENT DOCUMENTS

JP    2014150957 A    8/2014
WO   2016032717 A1    3/2016

OTHER PUBLICATIONS

Translation of Igarashi et al. JP2014150957 (Year: 2014).*
(Continued)

*Primary Examiner* — Peter Hoang

(57) ABSTRACT

The present disclosure describes an image rendering technique that provides a simulated light source positioned within a three dimensional (3D) data set for rendering two dimensional projection images of the 3D data set. The simulated light source may be positioned anywhere inside or outside the 3D data set, including within a region of interest. The simulated light source may be a multidirectional light source. A user may select a position of the simulated light source via a user interface. A user may select an in-plane position of the simulated light source and an image processor and/or volume renderer may automatically calculate a
(Continued)

depth position to maintain a distance between the simulated light source and a surface of a region of interest in the 3D data set.

15 Claims, 15 Drawing Sheets

(51) Int. Cl.
*G06F 3/0488* (2013.01)
*G06T 15/08* (2011.01)

(56) References Cited

U.S. PATENT DOCUMENTS

| | | |
|---|---|---|
| 2008/0009738 A1* | 1/2008 | Li .......................... G06T 19/00 600/458 |
| 2010/0198009 A1 | 8/2010 | Farr et al. |
| 2012/0069020 A1 | 3/2012 | Smith-Casem |
| 2012/0101388 A1 | 4/2012 | Tripathi |
| 2016/0030007 A1 | 2/2016 | Tsujita |

OTHER PUBLICATIONS

International Search Report and Written Opinion for International Application No. PCT/EP2017/077535, filed Oct. 27, 2017, 14 pages.

* cited by examiner

SYSTEMS AND METHODS FOR SIMULATED LIGHT SOURCE POSITIONING IN RENDERED IMAGES

This application is the U.S. National Phase application under 35 U.S.C. § 371 of International Application No. PCT/EP2017/077535, filed on Oct. 27, 2017, which claims the benefit of European Application Serial No. 16306455.3, filed Nov. 7, 2016. These applications are hereby incorporated by reference herein.

BACKGROUND

In medical imaging, images may be rendered in real time or post-data set acquisition. The images may be two dimensional (2D) slices or planes acquired within a volume or the images may be three dimensional (3D) volumes. 3D volume rendering techniques may involve casting virtual rays into an imaged 3D volume to obtain a 2D projection of the data that may be displayed in a final rendered image. The data may include anatomic structures within the imaged volume. When rays are cast from a virtual observer's position towards a region of interest within the imaged volume, various anatomic structures may be interposed along the line of sight. Incoming light direction drives the appearance of shadows and reflections on the surfaces of the anatomic structures. Use of a simulated light source in rendering the image may provide a user with a sense of depth and how the various anatomic structures are arranged in the 3D volume. One or more anatomic structures may block or otherwise interfere with obtaining a clear image of the region of interest. The user may rotate the 3D volume, which may change the position of the virtual observer and/or simulated light source relative to the 3D volume. A new 2D projection of the data may be rendered. Shadows and other lighting effects from the simulated light source may shift based on the rotation of the 3D volume, providing the user with additional information on depth and arrangement of anatomical features.

For a given 3D image data set, image rendering techniques are used to produce a 2D image from a given viewpoint by making assumptions about the optical properties of tissue being imaged under a light source of a predefined color and intensity. Currently, image rendering techniques for ultrasound imaging systems rely on a directional light source located at a fixed distance or infinity. The incoming light direction may be presented to a user by an arrow on a trackball-controlled dedicated sphere widget. In addition to rotating the 3D volume, the user may change the direction of incoming light from the simulated light source.

FIG. 1 is a schematic illustration of an example of an existing image rendering technique 100. A 3D data set 130 may have been acquired by an ultrasound probe or other imaging technique. The 3D data set 130 may include data corresponding to a 3D volume in a body. The 3D data set 130 may include a region of interest 135. The region of interest 135 may be a portion of an object (e.g., wall of blood vessel, valve of heart) or may be an entire object (e.g., tumor, fetus). When rendering an image of the 3D data set 130 including the region of interest 135, a simulated light source may be used to provide shadows and reflections on one or more surfaces within the 3D data set 130, for example, a surface 136 of the region of interest 135, which may provide depth perception for a user. The simulated light source may be a directional light source 105. The directional light source 105 may transmit light only in a direction indicated by arrow 115. The user may be permitted to select a position of the directional light source 105 at a fixed distance 110 from the 3D data set 130. A 2D projection of the 3D data set 130 may be rendered relative to display image plane 120, based on a virtual observer observing the 3D data set 130 from a viewpoint indicated by arrow 125. Display image plane 120 may be aligned with the X-Y plane of the 3D data set 130. Arrow 125 may be perpendicular to image plane 120. That is, a virtual observer may be considered to be "looking" through the image plane 120 at the 3D data set 130 through the depth of the 3D data set 130 indicated by the Z-axis. The 2D projection at display image plane 120 of the 3D data set 130 may be provided as an image to a user on a display.

Although the user may move the directional light source 105 about the 3D data set 130, locating the directional light source 105 outside of a rendered volume may cause object self-shadowing and make it difficult to illuminate structures of the region of interest 135. Details of the volume and/or region of interest 135 may be obscured. Anatomic details inside concave cavities may not be visible without cropping of the 3D data set 130 or other significant adjustments.

FIG. 2 is an example of an image 200 rendered from a 3D data set using an external directional light source. The image 200 displays a fetus 205 within a uterus 210. Many anatomical structures of the fetus 205 are obscured by shadows cast by the uterus 210 based on an image rendering technique using a directional light source located outside the uterus 210. This may inhibit the user, which may be a sonographer, obstetrician, or other clinician, from making a diagnosis or being able to navigate within the volume defined by the 3D data set.

JP2014150957 discloses an ultrasonic diagnostic apparatus with a light source setting section, a rendering control section, and a display control section. The light source setting section, on the basis of the shape of a region of interest which is included in three-dimensional image data collected by an ultrasonic probe, sets a direction in which the region of interest is depicted. The rendering control section controls to generate the rendering image in which the region of interest is depicted in the direction set by the light source setting section. The display control section controls to display the rendering image on a display section.

WO2016/032717 discloses a method, system and medical imaging device include accessing a 3D medical imaging dataset and generating a volume-rendered image from the 3D medical imaging dataset. Generating the volume-rendered image includes calculating a shading for the volume-rendered image based on a first light source, a second light source, and a third light source. The second light source and the third light source are both positioned differently than the first light source. The method, system, and medical imaging device also include displaying the volume-rendered image.

SUMMARY

An imaging system according to at least one embodiment of the disclosure may include an ultrasound probe which may be configured to receive ultrasound echoes from a subject to image a volume of the subject, a scan converter which may be configured to generate a three dimensional (3D) data set from the ultrasound echoes; a volume renderer which may be configured to calculate surface shading information of a first surface of the 3D data set based, at least in part, on a location of a simulated light source, and render a two dimensional (2D) projection image of the 3D data set which includes the shading information; and a user interface which may include a display which may be configured to display the 2D projection image, and an input device that may include a user interface element that may be configured to receive first user input indicative of an in-plane position of the simulated light source within a projection plane of the 2D projection image, and the volume renderer may be further configured to automatically position, responsive to the user input, the simulated light source at a location corresponding to the in-plane position and a depth position determined by the volume renderer.

A method according to at least one embodiment of the disclosure may include receiving a selection of a simulated light source for rendering a 2D projection image of a 3D data set, wherein the 3D data set may be constructed from ultrasound echoes received from a volume of a subject, receiving an indication, responsive to user input, of an in-plane position of the simulated light source in a plane corresponding to a projection plane of the 2D projection image, automatically determining a depth position of the simulated light source on an axis normal to the projection plane, calculating surface shading information of a surface of the 3D data set based, at least in part, on the in-plane and depth positions; and rendering the 2D projection image including the shading information on a display.

DETAILED DESCRIPTION

Figure 1:
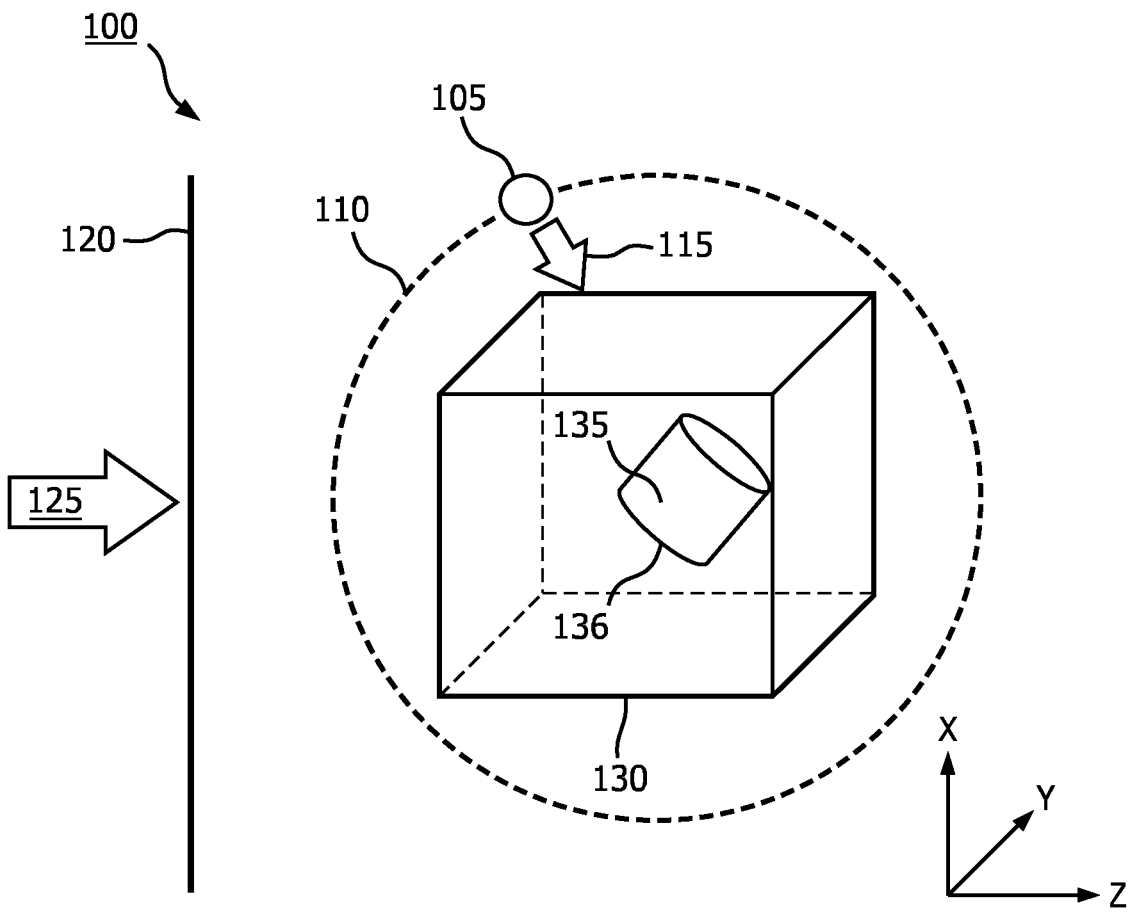
FIG. 1 is a schematic illustration of an image rendering technique using an external directional light source.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In some applications, it may be desirable to render an image from a 3D data set using a simulated light source positioned within the 3D data set. In some applications, it may be desirable to render an image from a 3D data set using a simulated light source within a region of interest within the 3D data set. In some applications, it may be desirable for the simulated light source to be a multidirectional light source. For example, the simulated light source may be modeled as a sphere that projects light from the entire surface of the sphere in all directions. In another example, the simulated light source may be modeled as a point source that projects light in all directions. Allowing a user to place the simulated light source within the 3D data set may provide rendered images that are less obscured by shadows and/or other artifacts that are generated when an image is rendered with a simulated directional light source located outside the 3D data set. Compared to lighting with an external light source, the close-range lighting may provide better local depth perception of shape and curvature of objects. An image rendered with a simulated light source within the 3D data set may provide an image that is easier for a clinician or other user to interpret. This may improve the ability of the clinician or other user to make a diagnosis and/or navigate within the 3D data set.

In an illustrative example, a clinician may conduct an ultrasound exam on a patient and acquire a 3D data set from the patient (e.g., a fetus in utero). The imaging system may render an image of a 2D projection of the 3D data set with a simulated multidirectional light source. The clinician may move the light source within the 3D data set, and the imaging system may adjust the rendered image based in part on the new position of the light source. For example, the clinician may touch a touch screen displaying the rendered image along with a visual cue for the light source (e.g., orb, square, X, etc.) and "drag" the light source to different positions within the image. The clinician may move the light source to investigate different areas of interest. Continuing with this example, the clinician may move the light source to highlight contours of the face of the fetus to check for a cleft pallet. The clinician may then move the light source to illuminate the spine to check for deformities. The clinician may choose to control the location of the light source in the image plane (e.g., an in-plane position, X-Y plane position) as well as the depth of the light source in the 3D data set (e.g., along an axis perpendicular to a plane of the in-plane position, along a Z-axis) or the imaging system may automatically set the depth position of the light source in the 3D data set. The clinician may control the light source during the ultrasound exam or during review of stored images after an exam.

Figure 3:
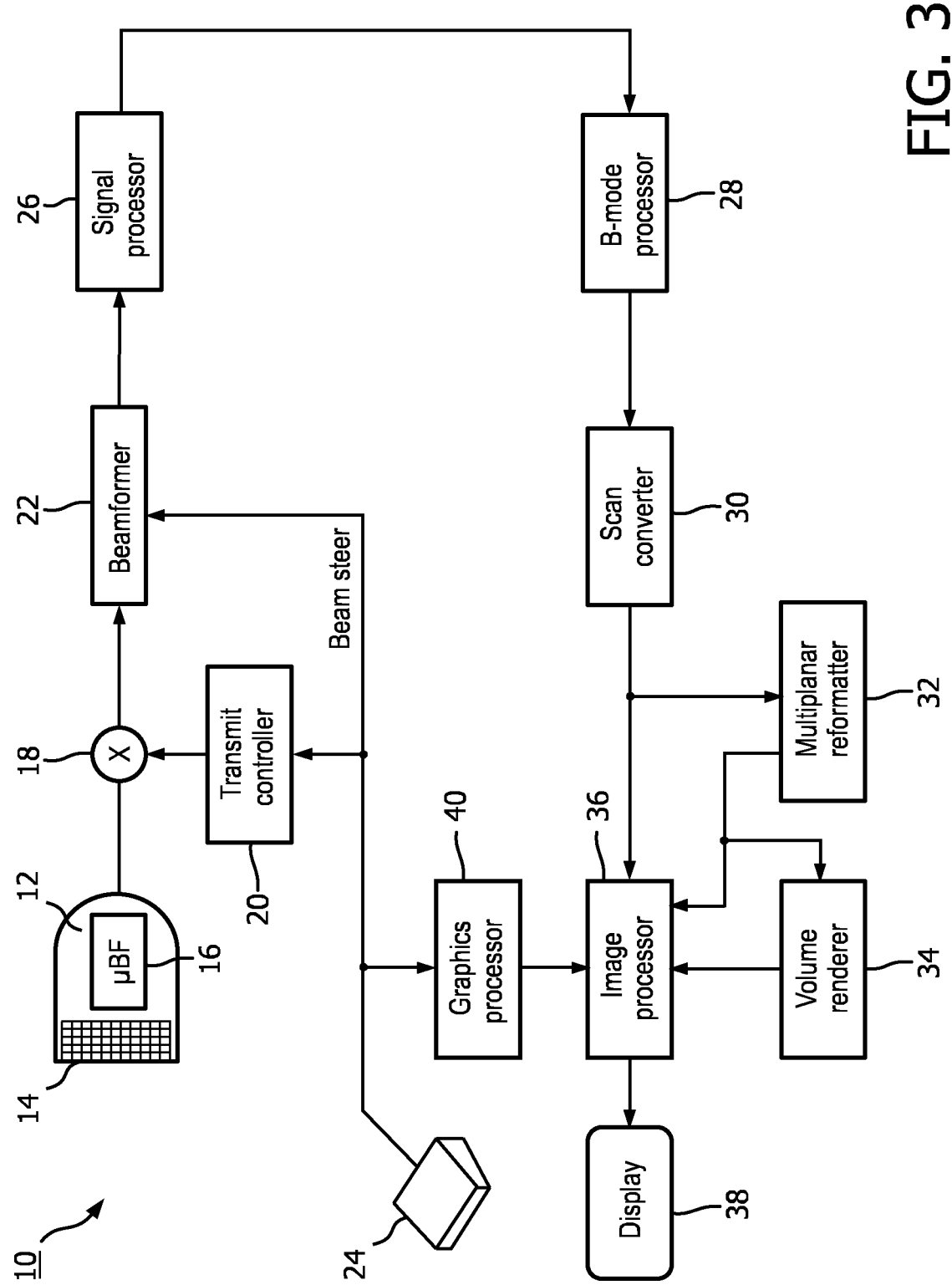
FIG. 3 is a block diagram of an imaging system according to embodiments of the present disclosure.

FIG. 3 shows a block diagram of an ultrasound imaging system 10 constructed in accordance with the principles of the present disclosure. Although an ultrasound imaging system is shown in explanatory examples of embodiments of the invention, embodiments of the invention may be practiced with other medical imaging modalities. Other modalities may include, but are not limited to, magnetic resonance imaging and computed tomography. The ultrasound imaging system 10 in FIG. 3 includes an ultrasound probe 12 which includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the ultrasound probe 12 which controls transmission and reception of signals by the transducer elements in the array. In this example, the microbeamformer 16 is coupled by the probe cable to a transmit/receive (T/R) switch 18, which switches between transmission and reception and protects the main beamformer 22 from high energy transmit signals. In some embodiments, for example in portable ultrasound systems, the T/R switch 18 and other elements in the system can be included in the ultrasound probe rather than in a separate ultrasound system base. The transmission of ultrasonic beams from the transducer array 14 under control of the microbeamformer 16 is directed by the transmit controller 20 coupled to the T/R switch 18 and the beamformer 22, which receive input from the user's operation of the user interface or control panel 24. The user interface 24 may include one or more input devices including one or more user interface elements (e.g., buttons, track ball, rotary encoder, or a soft control provided on a touch screen). In some embodiments, one or more of the user interface elements may include one or more graphical user interface (GUI) elements, which may be provided on a touch screen. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B-mode processor 28, which can employ amplitude detection for the imaging of structures in the body. The signals produced by the B-mode processor 28 are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. In some embodiments, the scan converter 30 may generate a 3D data set from the echo signal. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.). In some embodiments, the volume renderer 34 may receive input from the user interface 24. The input may include the given reference point (e.g., viewpoint of a virtual observer), position of a simulated light source, and/or properties of the simulated light source for the rendered projected image. In some embodiments, the volume renderer 34 may determine an in-plane and/or depth position of the simulated light source automatically. In some embodiments, the volume renderer 34 may calculate surface shading information for one or more surfaces in the 3D data set based at least in part, on the position and/or properties of the simulated light source. The 2D or 3D images are coupled from the scan converter 30, multiplanar reformatter 32, and volume renderer 34 to an image processor 36 for further enhancement, buffering and temporary storage for display on an image display 38. The image processor 36 may render visual cues for the simulated light source (e.g., orb, halo) in some embodiments. In some embodiments, the visual cues may be rendered by the volume renderer 34. The graphics processor 40 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

According to an embodiment of the disclosure, the ultrasound probe 12 may be configured to receive ultrasound echoes from a subject to image a volume of the subject. The scan converter 30 may receive the ultrasound echoes and generate a 3D data set. As described above, the ultrasound echoes may be pre-processed by the beamformer 22, signal processor 26, and/or B-mode processor prior to being received by the scan converter 30. The 3D data set may include values for each point (e.g., voxel) in the imaged volume. The values may correspond to echo intensity, tissue density, flow rate, and/or material composition. Based on the values in the 3D data set, the scan converter 30 and/or volume renderer 34 may define one or more surfaces within the imaged volume. The surfaces may represent a boundary between two different objects (e.g., fetus and uterus) or materials (e.g., bone and muscle), or regions (e.g., different flow rates in a vessel) within the imaged volume. In some embodiments, the surfaces may be isosurfaces.

When rendering a 2D projection image of the 3D data set, the volume renderer 34 may receive a location of a simulated light source relative to the 3D data set. In some embodiments, the location of the simulated light source may be pre-programmed by the imaging system 10. The simulated light source may default to a pre-programmed location, e.g., upon activation of a volume rendering mode, and in some cases the light source may be movable by the user while in the volume rendering mode. In some embodiments, the location of the simulated light source may be received via user interface 24, which may include input devices having one or more input elements configured to receive user input. For example, the user interface 24 may include a touch screen with a graphical user interface (GUI) that allows a user to set a location of the simulated light source anywhere within and/or proximate to the 3D data set. As an example, the graphical user interface (GUI) may provide one or more GUI elements that enable the user to set the location of the simulated light source. In some examples, a GUI element (e.g., a light orb) may additionally provide a visual cue as to the location of the light source in relation to the volume. In other examples, the GUI element may be an input widget whereby the user may be able to specify the location (e.g., specify X, Y, Z coordinates) of the light source. Other examples of GUI elements may be used. In yet further examples, the user input may be received via a mechanical control (e.g., a trackball or a rotary encoder on a control panel) which in the volume rendering mode may be specifically associated with and configured to generate manipulation commands for moving the light source. In some embodiments, only the in-plane position (e.g., X and Y coordinates) may be received via the user interface 24, and the volume renderer 34 may automatically determine a depth position (e.g., Z coordinate) of the simulated light source. The depth position may be determined based, at least in part, on a pre-set distance from a surface in the 3D data set. The pre-set distance may be pre-programmed and/or user configurable. For example, the pre-set distance may be stored in memory and the volume renderer may be programmed to use the pre-set distance as a default value when determining the depth dimension default unless the default value is modified by a user. In some embodiments, the user interface may provide a user interface element configured to receive user input for specifying the pre-set distance.

The volume renderer 34 may calculate surface shading information for one or more surfaces within the 3D data set, based, at least in part, on the location of the simulated light source relative to the 3D data set. The surface shading information may include information regarding the brightness of any given pixel representing a surface of the 3D dataset in a rendered 2D projection image, which information may provide three-dimensionality to the otherwise 2D rendered image. In addition to the location of the light source relative to the surface, the surface shading information may be based on properties of the volume adjacent to the surface (e.g., the value of voxels interposed between the light source and the surface). For example, when calculating the shading information for a given surface, the volume renderer 34 may take into account the density of tissue interposed between the simulated light source and the rendered outer surface. When the simulated light source is located in front of a surface of the imaged volume, only zero-value voxels may be interposed between the light source and the surface and an illuminated region on the surface may have a high luminosity or brightness than in instances in which the simulated light source is behind the surface and thus spaced from the surface by non-zero value voxels. Light transmittance through the zero-value voxels of the regions surrounding the rendered 3D dataset may be approximated, by known light simulation techniques, to be similar to light transmittance through air, thus light transmittance through non-zero value voxels may be reduced to approximate transmittance through tissue which is denser than air. Thus, when the simulated light source is located behind a surface enclosing a volume of the 3D data set having a density higher than a surrounding volume, the surface shading information calculated by the volume renderer 34 may be different than when the simulated light source is located in front of the surface. For example, the surface shading information may include fewer reflections and appear to "glow" from within when the simulated light source is located behind the surface while the surface shading information may be such that the surface appears more opaque when the simulated light source is located in front of the surface. As will be appreciated, density and other properties of an object positioned in front of a light source will affect the light transmittance through the object, thus the volume renderer 34 is configured to account for the density of material disposed between the light source and the surface being rendered.

Although reference is made to surface shading, the volume renderer 34 may or may not explicitly extract surfaces from the 3D dataset for calculating surface shading information. For example, the volume renderer 34 may calculate shading information for every voxel within the 3D dataset (e.g., volumetric shading). As previously mentioned, the shading information for each voxel may be based at least in part on the distance of the voxel from the simulated light source, the density of the voxel, and/or density of surrounding voxels. The resulting shading information for the 3D dataset may provide the appearance of 3D surfaces within the 3D dataset to a user. For simplicity, the shading information of surfaces of objects and/or areas of interest within the 3D dataset will be referred to as surface shading information without regard to the manner in which it is calculated by the volume renderer 34.

The surface shading information may be used by the volume renderer 34 to render the 2D projection image. The rendered 2D projection image may be provided by the volume renderer 34 to the image processor 36 in some embodiments. The rendered 2D projection image may be provided to the display 38 for viewing by a user such as a clinician. In some examples, the rendering by the volume renderer 34 and the resulting 2D projection image provided on the display 38 may be updated responsive to user inputs via the user interface 24, for example to indicate movement (e.g., translation or rotation) of the volume, movement of the simulated light source in relation to the volume, and/or other changes to parameters associated with the various rendering constructs in the rendering. For example, the volume renderer is configured, responsive to movement of the simulated light source via the user input, to automatically render the simulated light source at a location corresponding to the in-plane position and a depth position determined by the volume renderer. In some embodiments, the depth position is set based at least in part on contours of the first surface.

Figure 4:
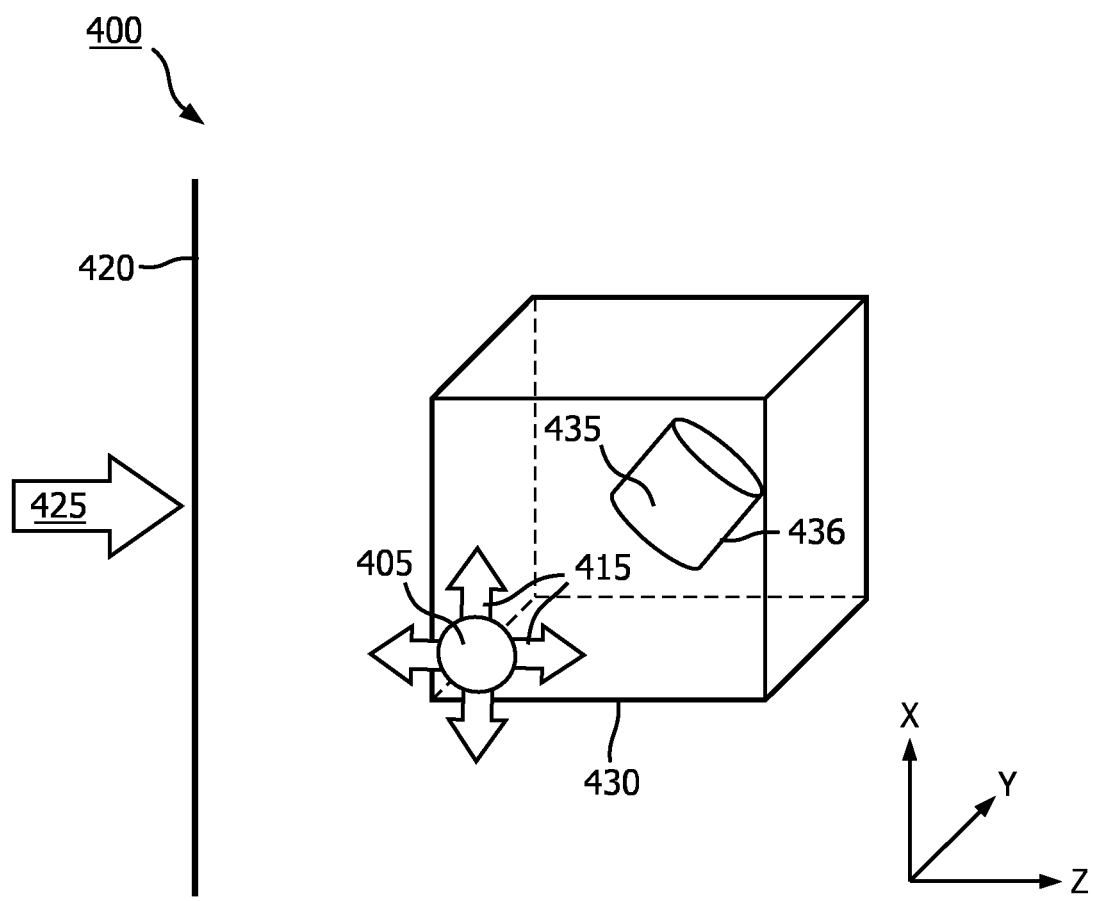
FIG. 4 is a schematic illustration of an image rendering technique using a simulated light source according to an embodiment of the present disclosure.

FIG. 4 is a schematic illustration of an image rendering technique 400 according to an embodiment of the disclosure. In some embodiments, the image rendering technique 400 may be performed by an imaging system such as ultrasound imaging system 10. A 3D data set 430 may have been acquired by an ultrasound probe, such as ultrasound probe 12 shown in FIG. 3. In other examples, the 3D dataset 430 may have been acquiring using a different medical imaging modality (e.g., CT, MRI, etc.). The 3D data set 430 may include data corresponding to a 3D volume in a body. The 3D data set 430 may include a region of interest 435. The region of interest 435 may be a portion of an object (e.g., wall of blood vessel, valve of heart) or may be an entire object (e.g., tumor, fetus). In some embodiments, the 3D data set 430 may include multiple regions of interest 435. A 2D projection image of the 3D data set 430 may be rendered relative to display image plane 420, based on a virtual observer observing the 3D data set 430 from a viewpoint indicated by arrow 425. Display image plane 420 may be aligned with an X-Y plane. The vector indicated by arrow 425 may pass through image plane 420. That is, a virtual observer may be considered to be "looking" through the image plane 420 at the 3D data set 430 through the depth of the 3D data set 430 indicated by the Z-axis, which is orthogonal to the X-Y plane. Although shown perpendicular to image plane 420, arrow 425 may be at some other angle relative to image plane 420 (e.g., 10, 30, 45 degrees). The 2D projection image at display image plane 420 of the 3D data set 430 may be provided as an image to a user on a display, such as display 38 shown in FIG. 3.

When rendering an image of the 3D data set 430 including the region of interest 435, a simulated light source 405 may be used to calculate surface shading information to render shadows and reflections on one or more surfaces within the 3D data set 430, for example, a surface 436 of the region of interest 435, which may provide depth perception for a user. The surface shading information may be based, at least in part, on the position of the simulated light source 405 relative to the 3D data set 430 and/or region of interest 435. In some embodiments, the simulated light source 405 may be a multidirectional light source. The light source 405 may transmit light in all directions as indicated by arrows 415. Unlike the light source 105 shown in FIG. 1, the user may be permitted to select a position of the light source 405 outside of or anywhere within the 3D data set 430. As shown in the embodiment illustrated in FIG. 4, the light source 405 is within the 3D data set 430 at a depth less than a depth of the region of interest 435. That is, the light source 405 is at a depth along the Z-axis between the region of interest 435 and the virtual observer looking from a direction indicated by arrow 425. In some embodiments, the user may select a position of the simulated light source 405 in the image plane 420 and the imaging system may automatically determine a depth position of the simulated light source 405.

Figure 2:
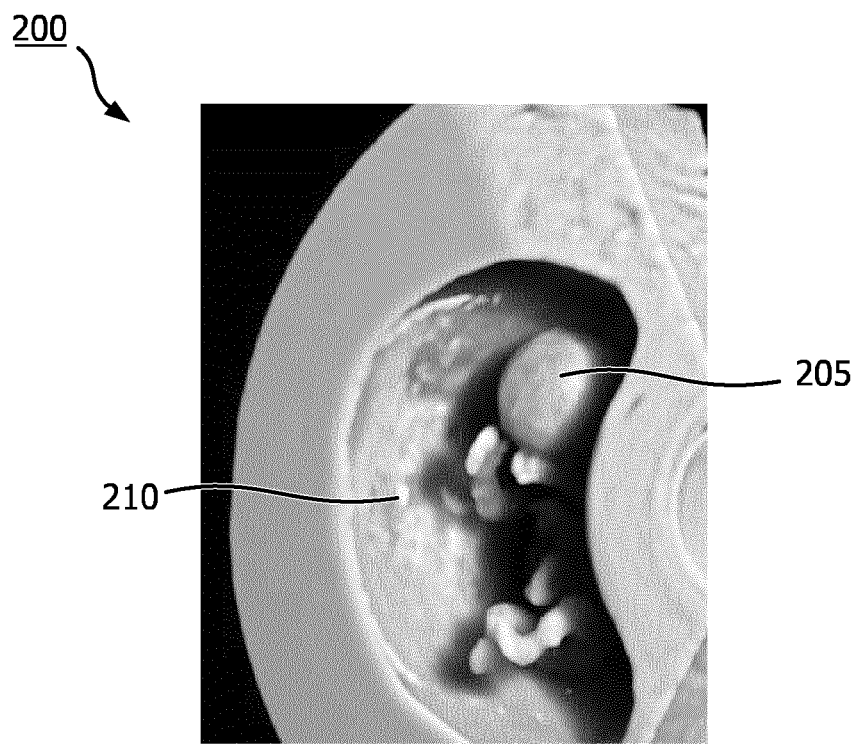
FIG. 2 is an example of a rendered image using the image rendering technique shown in FIG. 1.
Figure 5:
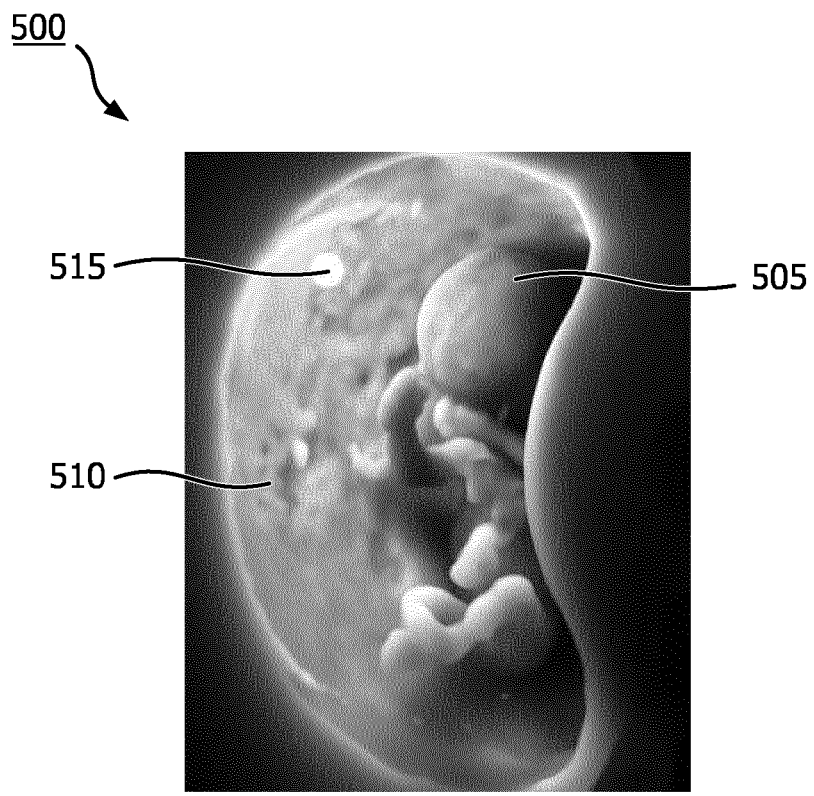
FIG. 5 is an example of a rendered image using the image rendering technique shown in FIG. 4.

FIG. 5 is an example image 500 rendered using the image rendering technique 400 shown in FIG. 4. The image 500 is rendered from the same 3D data set as image 200 shown in FIG. 2, a fetus 505 within a uterus 510. In some embodiments, the simulated light source may be rendered as an emissive material in the image. In the example shown in image 500, the simulated light source is rendered as a glowing orb 515. The glowing orb 515 is rendered within the 3D data set within the uterus 510. As a result, the uterus 510 does not cast shadows that obscure the fetus 505. In contrast with the fetus 205 in FIG. 2, the left arm, right shoulder, and torso of fetus 505 may be discerned. These same features are obscured by uterine shadows in the image 200 shown in FIG. 2.

Figure 6:
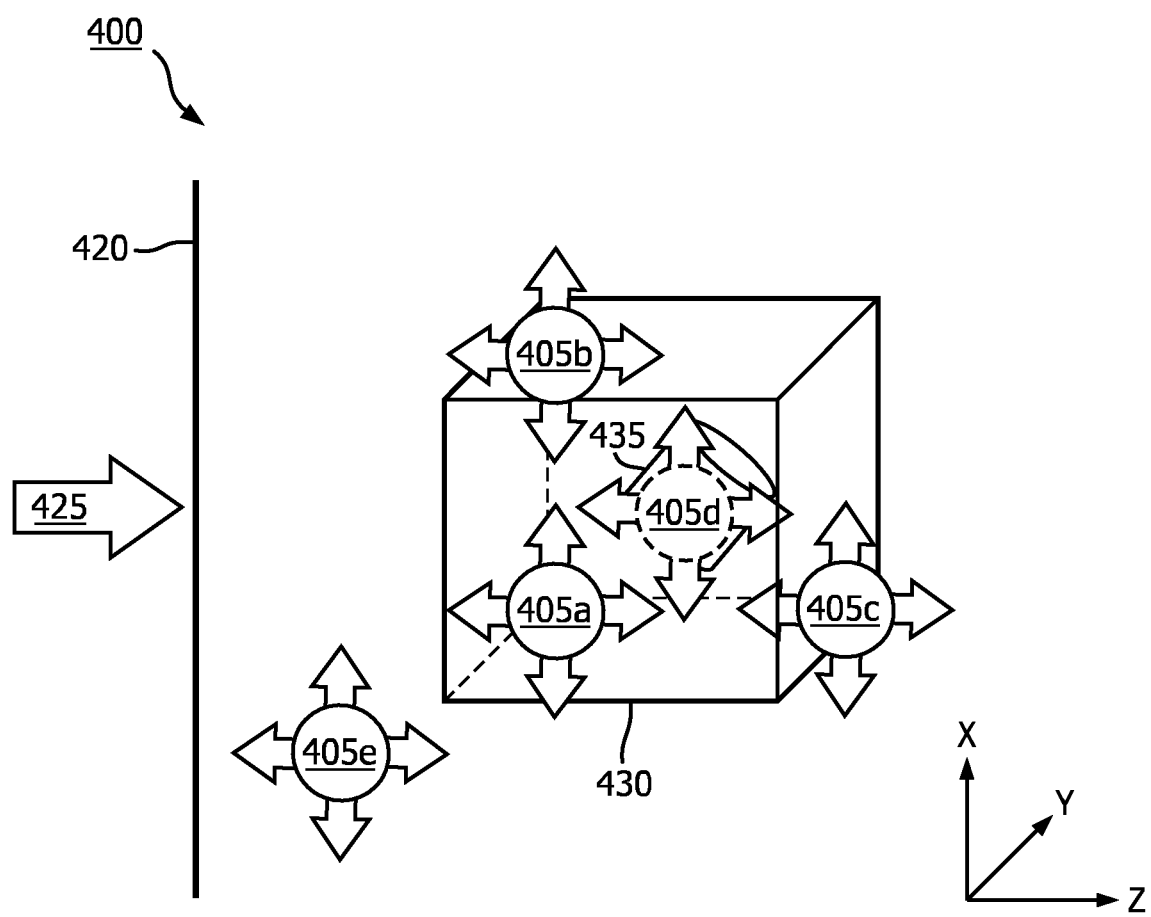
FIG. 6 is a schematic illustration of the image rendering technique shown in FIG. 4.

As mentioned previously, the light source 405 is not limited to a set distance from the 3D data set 430. FIG. 6 is a schematic illustration of a variety of example possible positions of the light source 405a-e according to embodiments of the disclosure. As shown in FIG. 6, the light source 405 may be rendered at varying positions in the image plane 420 (e.g., different positions on the X-Y plane) and at different depths within the 3D data set 430 (e.g., along the Z-axis). For example, the light source 405a is in the position shown in FIG. 4, and light source 405b is at the same depth as light source 405a, but at a different point in image plane 420 in the 3D data set 430. Positioning the light source 405 in front of the region of interest 435 may allow a user to discern features on the surface 436 of the region of interest 435 and/or surrounding area. Light source 405c is at both a different point on the image plane 420 and at a different depth in the 3D data set 430. As shown in FIG. 6, light source 405c is at a deeper depth than the region of interest 435 with reference to the image plane 420. Positioning the light source 405 behind the region of interest 435 may allow the user to make at least a qualitative determination of the thickness and/or density of the region of interest 435. The light source 405 may even be placed within the region of interest 435, as shown by light source 405d. Positioning the light source 405 within the region of interest 435 may allow the user to observe more subtle contours and depths of different components within the region of interest 435. The position of the light source 405 is not limited to the 3D data set 430. Light source 405e shows an example of a position outside the 3D data set 430. The example positions are shown for explanatory purposes only, and the light source 405 is not limited to the positions shown in FIG. 6. There may be alternative and/or additional advantages to different positions of the light source 405 than those described above. For example, the user may position the light source 405 to avoid casting shadows from other anatomy and/or portions of the region of interest 435.

Although not shown in FIG. 6, the simulated light source 405 may be a directional light source rather than a multidirectional light source. In some embodiments, a user may be able to toggle between multidirectional and directional modes. A directional light source within the 3D data set 430 may be desirable in some applications. For example, a user may want to highlight a particular area within the 3D data set while minimizing the illumination to other areas, which may reduce distractions (e.g., a "spotlight" effect).

Figure 7:
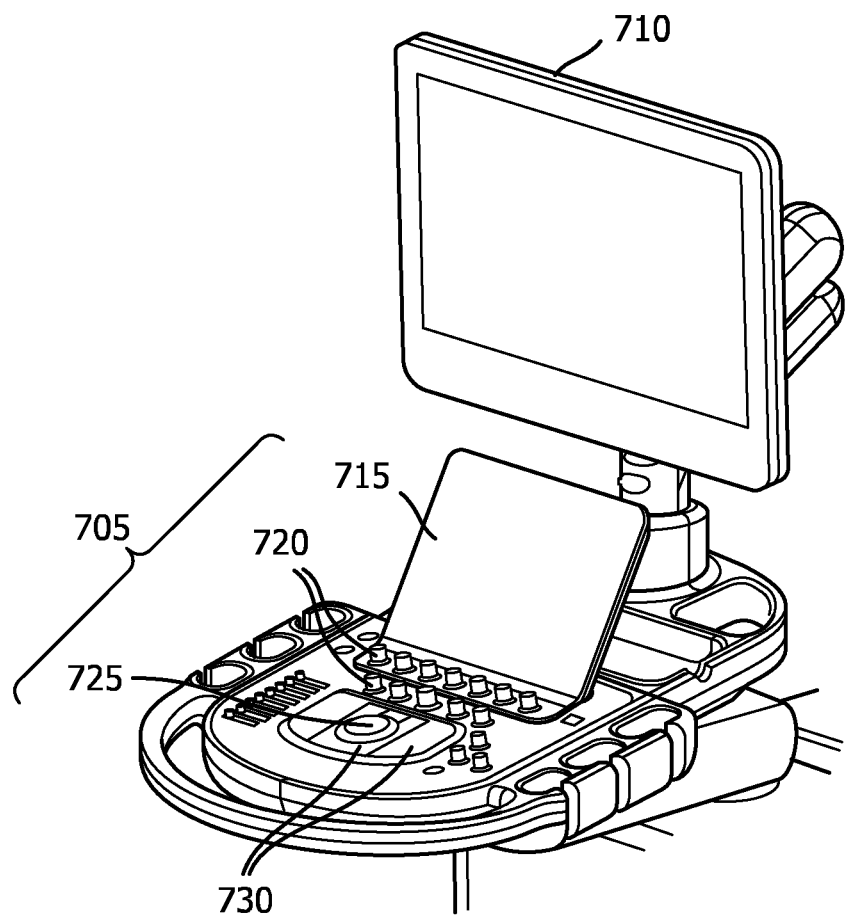
FIG. 7 is an illustration of a user interface according to an embodiment of the disclosure.

FIG. 7 is an illustration of a portion of an ultrasound system 700 that may be used to implement an embodiment of the disclosure. The ultrasound system 700 may include a user interface 705 and a display 710. In some embodiments, user interface 705 may be used to implement user interface 24 shown in FIG. 3. The display 710 may be used to implement display 38 shown in FIG. 3 in some embodiments. The user interface 705 may include one or more input devices including one or more user interface elements. For example, user interface 705 may include a touch screen 715, one or more rotary controls 720, a track ball 725, and buttons 730. In some embodiments, the buttons 730 may include arrow keys and/or a QWERTY keyboard. In some embodiments, the display 710 may also be part of the user interface 705. For example, the display 710 may be implemented using a touch screen. A user may have the option of using the display 810, the touch screen 715, and/or other controls included in the user interface 705 to position the simulated light source in a rendered image and/or control other properties of the simulated light source (e.g., directional vs. multidirectional, intensity, color). In yet further examples, the input device may include a touchless interface configured to receive user inputs without the user physically contacting the touch screen or mechanical controls of the system 700.

A user may control the position of the simulated light source in a rendered image via a user interface such as the user interface 705 shown in FIG. 7. In some embodiments, the user may use the track 725 ball and the rotary control 720. The user may select an in-plane position (e.g., an X-Y coordinate) on the image plane with the track ball 725 and select a depth position (e.g., a coordinate on the Z-axis) with the rotary control 720 to set the position of the simulated light source. In some embodiments, an individual rotary control may be provided for each degree of freedom (e.g., an X-axis control, a Y-axis control, and a Z-axis control) to set the position of the simulated light source. In some embodiments, the user may use buttons 730, such as arrow keys, to select a position (e.g., X-Y-Z coordinate) of the simulated light source. In some embodiments, the user may select an in-plane position of the simulated light source and the imaging system may automatically determine a depth position of the simulated light source for the selected in-plane position.

In some embodiments, the user interface 705 or an input element of the user interface includes a graphical user interface (GUI). For example, the display 710 and/or touch screen 715 may include a GUI. In some embodiments, the user may use the touch screen 715 to position the simulated light source. A variety of gestures on the touch screen 715 may be used to select a position of the simulated light source. For example, the user may tap the touch screen 715 at a location to set the in-plane position and/or touch a rendered light orb in the image displayed on the touch screen 715 and "drag" it to an in-plane position by moving their finger along the touch screen 715. Each point on the touch screen 715 may coincide with each point of the image plane of a rendered 2D projection image. These gestures are provided only as examples, and other gestures may be used to set the position of the simulated light source in the 3D data set (e.g., control buttons provided on touch screen). In some embodiments, a user may position the simulated light source using one or a combination of user input methods. For example, a user may set a position of the simulated light source using the touch screen and then "fine tune" the position using the track ball and/or rotary control. In some embodiments, the user interface 705 may include additional and/or alternative user input controls (e.g., slide control, motion sensor, stylus) for positioning the simulated light source. In some embodiments, the user may use the user interface 710 to control properties of the simulated light source. For example, a user may set an intensity and/or color of the light source.

Figure 8:
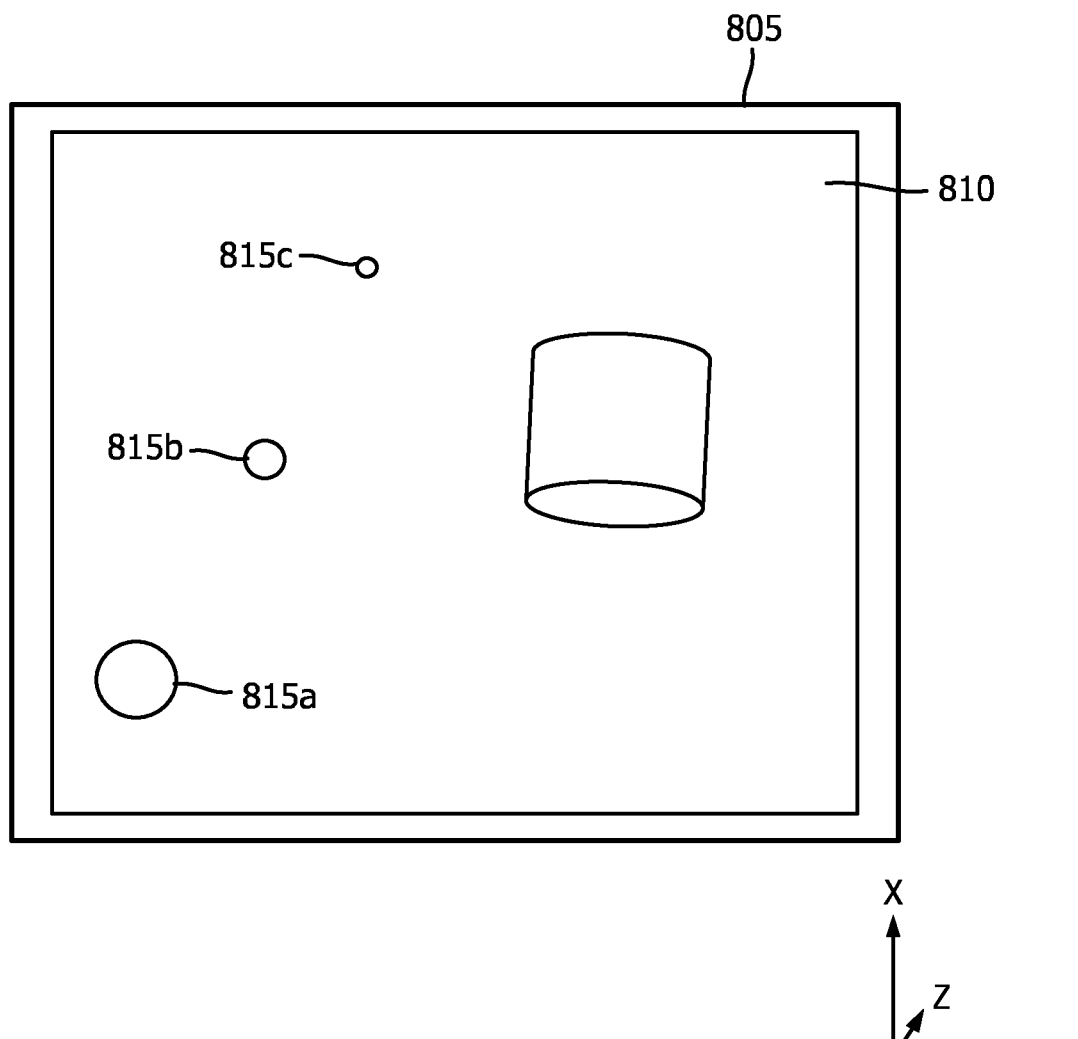
FIG. 8 is a schematic illustration of a display of a user interface according to an embodiment of the disclosure.

FIG. 8 is an illustration of a rendered image 810 on a display 805 according to an embodiment of the disclosure. Display 38 of FIG. 3 or display 710 of FIG. 7 may be used to implement display 805 in some embodiments. In some embodiments, the display 805 may include a GUI and the simulated light source 815 may be rendered with visual cues to assist a user in interpreting the position of the light source in the 3D data set. As shown in FIG. 8, the simulated light source 815 may be rendered in the image 810 as smaller in size as the light source is positioned farther away from the image plane in the 3D data set. In some embodiments, the image plane aligns with the display 805. As shown in FIG. 8, the light source 815 would appear to be moving further into the page. In this example, light source 815*a* is closest to the image plane and light source 815*c* is furthest from the image plane. Changing the size of the light source 815 in the image 810 may provide a visual cue indicating a depth of the light source 815 along the Z-axis in the 3D data set and may assist a user in interpreting the position of the light source within the 3D data set.

Figure 9:
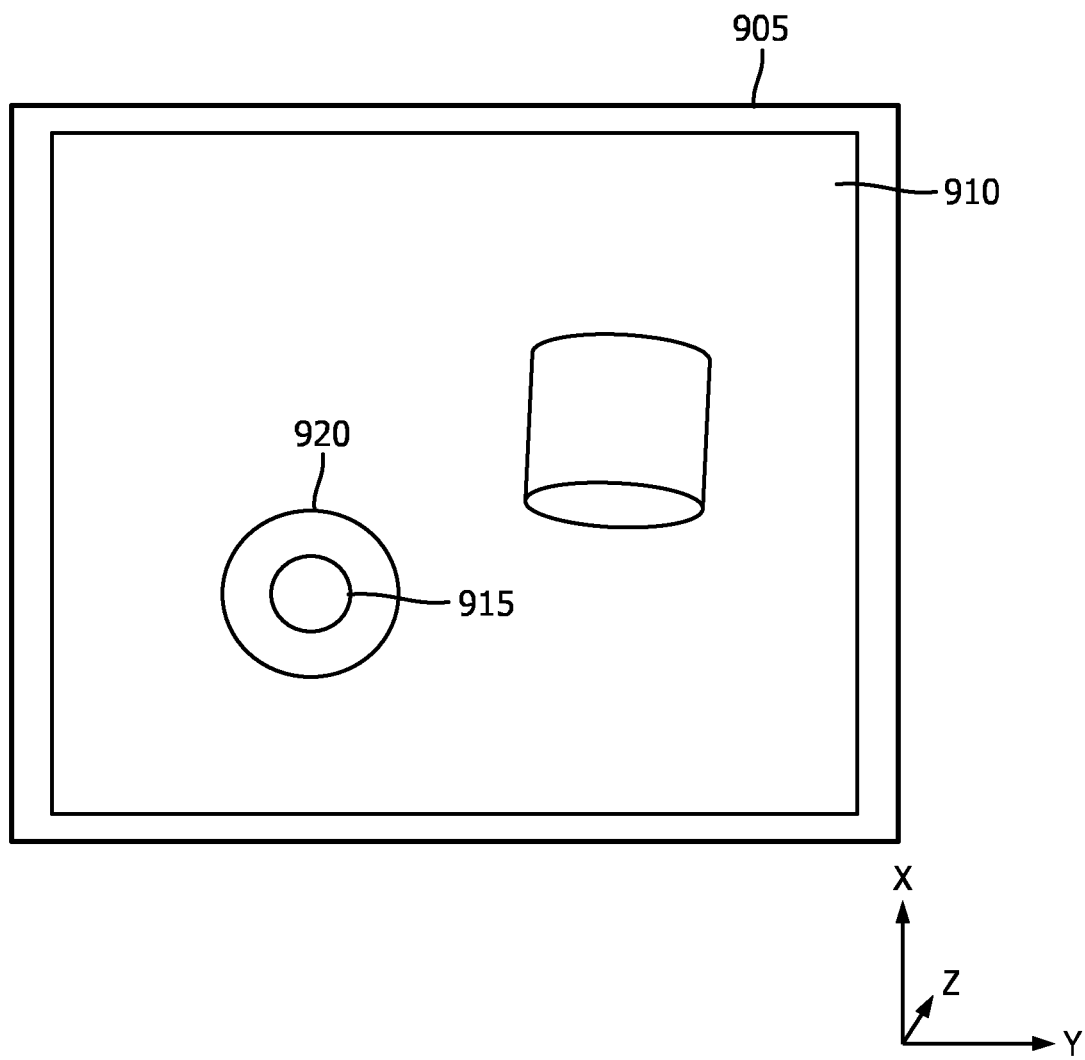
FIG. 9 is a schematic illustration of a display of a user interface according to an embodiment of the disclosure.

FIG. 9 is an illustration of a rendered image 910 on a display 905 according to an embodiment of the disclosure. Display 38 of FIG. 3 or display 710 of FIG. 7 may be used to implement display 905 in some embodiments. In some embodiments, the display 905 may include a GUI and the simulated light source 915 may be rendered in the image 910 with a halo 920. The halo 920 may allow a user to visually locate the light source 915 in the image 910. In some embodiments, the halo 920 may allow the user to locate the light source 915 when the light source 915 is positioned outside the field of view of the image 910. In some embodiments, a user may activate or deactivate the halo 920. That is, the user may control whether or not the halo 920 is rendered around the light source 915 in the image 910. In some embodiments, the halo 920 may automatically disappear after the light source 915 has been stationary for a period of time (e.g., half a second, two seconds, ten seconds). In some embodiments, the user may deactivate the visual cue of the light source 915. By deactivate, it is not meant that the user chooses to remove the lighting rendered from the light source 915 from the image 910, but that the user turns off the rendering of the visual cue of the light source 915 in the image 910 (e.g., the orb). In some embodiments, the rendering of the visual cue of the light source 915 may automatically disappear after the light source 915 has been stationary for a period of time (e.g., half a second, two seconds, ten seconds). Activating and deactivating the halo 920 and/or rendering of the light source 915 may allow for the user to observe the image 910 without interference from the visual cues for positioning the light source 915. Visual cues such as the orb and/or halo may be rendered by a volume renderer and/or image processor of an imaging system. For example, volume renderer 34 and image processor 36 of ultrasound imaging system 10 shown in FIG. 1 may be used to implement an embodiment of the disclosure.

A simulated light source that may be placed anywhere within and/or surrounding a 3D data set may provide additional illumination options for images rendered from the 3D data set. The simulated light source may be a multidirectional light source in some embodiments. These additional options may allow for rendering of images that are less prone to self-shadowing by other anatomical features and better definition of surfaces and/or thicknesses of tissues. However, in some applications, a user may not want to select an in-plane position and/or depth position of the simulated light source. The user may find navigating through the entire 3D data set to select a depth position time consuming and/or disorienting. In some embodiments, a user may choose an option that positions the simulated light source to a set distance from a region of interest and/or surface of the region of interest. That is, as a user moves the simulated light source through the image plane, the depth position of the simulated light source may automatically adjust based on contours of the surface of the region of interest such that a distance between the simulated light source and the region of interest and/or surface is maintained. For example, as a user moves the light source along an image of a spine, the light source may appear to "float" over the vertebrae, following the contours of the spine, remaining a set distance away from the spine. This automatic depth selection mode may be preferable when a user is conducting a cursory review of images and/or the user is less experienced with imaging systems.

Figure 10:
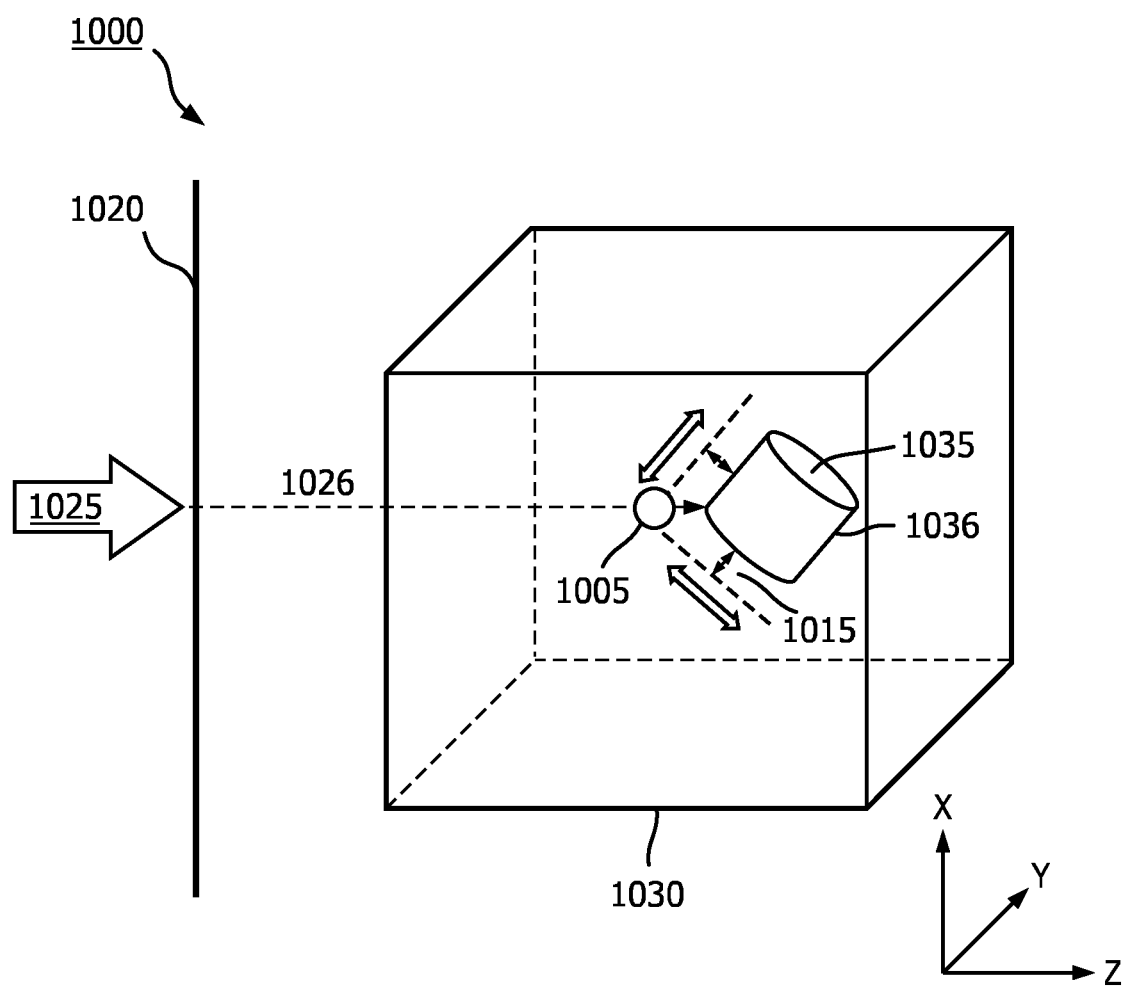
FIG. 10 is a schematic illustration of an image rendering technique according to an embodiment of the disclosure.

FIG. 10 is a schematic illustration of an image rendering technique 1000 according to an embodiment of the disclosure. In some embodiments, image rendering technique 1000 may be an embodiment of image rendering technique 400 wherein a depth position of a simulated light source is automatically determined by an imaging system. Image rendering technique 1000 may be performed by an imaging system such as ultrasound imaging system 10 shown in FIG. 3. A 3D data set 1030 may have been acquired by an ultrasound probe, such as ultrasound probe 12 shown in FIG. 3, or other input device. The 3D data set 1030 may include data corresponding to a 3D volume in a body of a subject. The 3D data set 1030 may include a region of interest 1035. The region of interest 1035 may be a portion of an object (e.g., wall of blood vessel, valve of heart) or may be an entire object (e.g., tumor, fetus). A 2D projection of the 3D data set 1030 may be rendered relative to display image plane 1020, based on a virtual observer observing the 3D data set 1030 from a viewpoint indicated by arrow 1025. Display image plane 1020 may be aligned with the X-Y plane. The vector indicated by arrow 1025 may pass through image plane 1020. That is, a virtual observer may be considered to be "looking" through the image plane 1020 at the 3D data set 1030 through the depth of the 3D data set 1030 indicated by the Z-axis. Although shown perpendicular to image plane 1020, arrow 1025 may be at some other angle relative to image plane 1020 (e.g., 10, 30, 45 degrees). The 2D projection at display image plane 1020 of the 3D data set 1030 may be provided as an image to a user on a display, such as display 38 shown in FIG. 3 or display 710 shown in FIG. 7.

In some embodiments, for a given position of a simulated light source 1005 in the display image plane 1020 (e.g., an X-Y coordinate), a ray 1026 may be cast into the 3D data set 1030 along arrow 1025. In some embodiments, arrow 1025 may be along an axis orthogonal to the image plane 1020 (e.g., along a Z-axis). The ray may be cast into the 3D data set 1030 until it finds a non-zero density point (e.g., voxel) that may be a portion of an imaged object in the 3D data set 1030 (e.g., a surface of an anatomical feature), such as a surface 1036 of the region of interest 1035. In some embodiments, the closest non-zero density point may be found by interpolation. A distance 1015 along the ray 1026 back towards the virtual observer away from the non-zero density point may be calculated. The imaging system may then position the simulated light 1005 source at a depth position that is distance 1015 from the surface 1036 of the region of interest 1035. The distance 1015 may be calculated by an image processor and/or a volume renderer in some embodiments. For example, image processor 36 and/or volume renderer 34 of ultrasound imaging system 10 shown in FIG. 3 may be used to implement an embodiment of the disclosure. In some embodiments, another processor may be used to calculate the distance 1015.

The distance 1015 may be pre-programmed or it may be set by the user. The distance 1015 may range from the equivalent of 1-10 millimeters in a volume from which the 3D data set 1030 was acquired. Larger or smaller distances may be used for the distance 1015 of the light source 1005 from the object, based in part on the application. For example, larger distances between the light source and the object may be used when viewing an entire fetus and smaller distances may be used when viewing a heart valve. In some embodiments, the distance 1015 of the light source 1005 from the surface 1036 of the region of interest 1035 may be based, at least in part, on a quality criterion. For example, a distance 1015 may be selected that minimizes the amount of shadowing in the vicinity of the target of the ray 1026 on the surface 1036 of the region of interest 1035. In another quality metric example, a distance 1015 may be selected that maximizes a dynamic range of lighting intensity in the 2D projection image.

The distance 1015 between the light source 1005 and region of interest 1035 may be maintained as the in-plane position of the light source 1005 is changed in the image plane 1020. That is, the depth position of the light source 1005 may automatically be adjusted. The imaging system may automatically "scan" the light source 1005 along the surface of the region of interest 1035 and/or a user may control the position of the light source 1005 in the image plane 1020 via a user interface (e.g., "drag" an orb rendered in the image via a touch screen, tap a desired location on a touch screen for the light source, manipulate a track ball, etc.). In some embodiments, the distance 1015 may be maintained while the region of interest 1035 is rotated relative to the image plane 1020 and/or the region of interest 1035 moves. For example, the region of interest 1035 may move over time when the 3D data set 1030 includes multiple 3D data sets corresponding to different periods of time (e.g., four dimensional image, real time imaging, time elapsed loop). In another example, the light source 1005 may remain stationary relative to a user and/or virtual observer while the 3D data set 1030 is rotated relative to the user and/or virtual observer.

In some embodiments, a volume renderer and/or image processor may determine the depth position of the simulated light source 1005. In some embodiments, the volume renderer and/or image processor may determine the shading information for the surface 1036 for rendering a 2D projection image at image plane 1020. In some embodiments, the volume renderer and/or image processor may dynamically determine the depth position of the simulated light source 1005, shading information, and render the 2D projection image as the in-plane position of the simulated light source 1005 is altered.

Figure 11A:
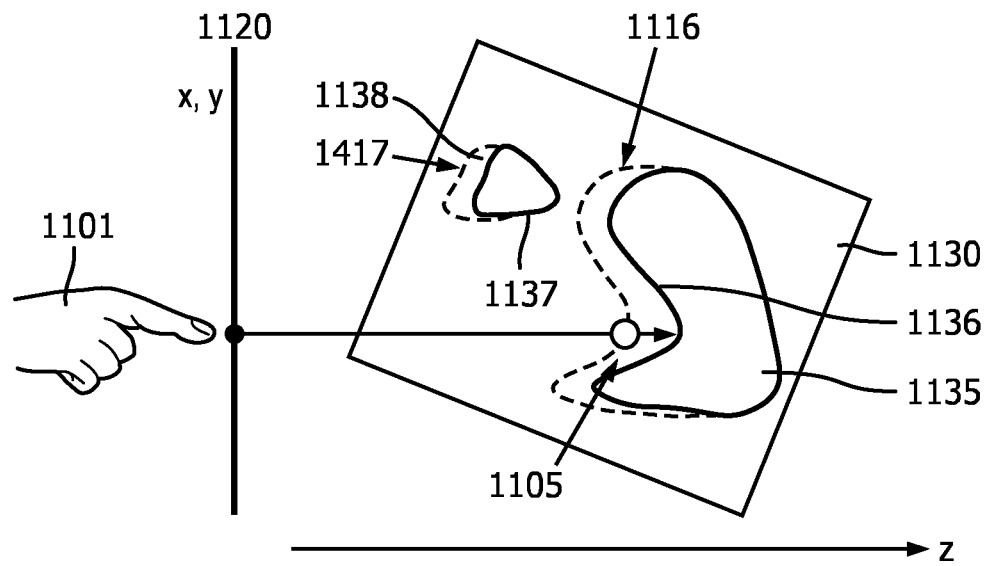
FIGS. 11A-B are schematic illustrations of a user positioning a light source according to an embodiment of the disclosure.
Figure 11B:
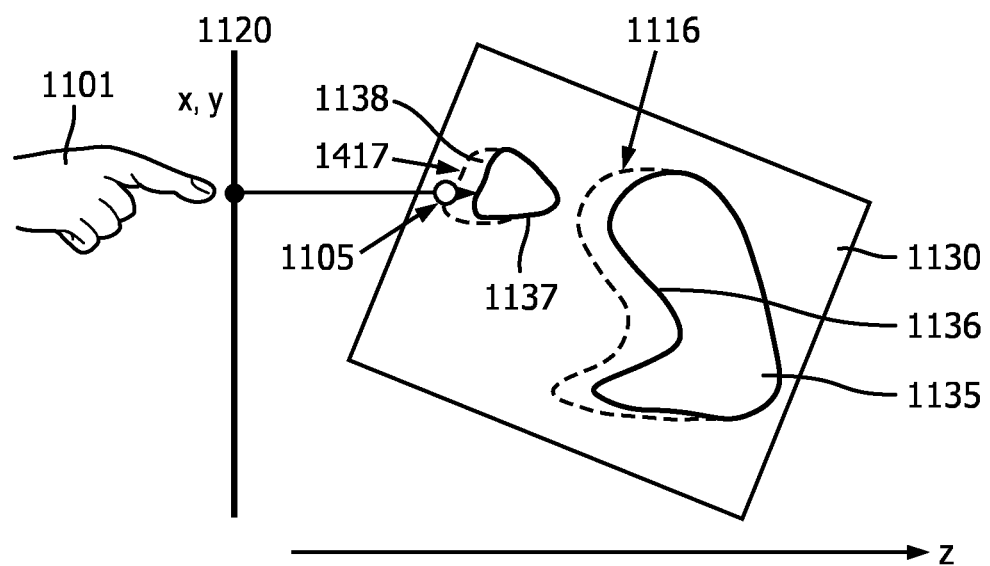

FIGS. 11*a-b* are schematic illustrations of a user positioning a simulated light source according to an embodiment of the disclosure. In some embodiments, the 3D data set may include multiple regions of interest (e.g., lesions along a vessel wall) and/or objects (e.g., vertebrae, interventional devices). A user may move a simulated light source to different positions in order to illuminate each of the regions of interest. When the image rendering technique 1000 is employed, a set distance between each region of interest and the simulated light source may be maintained automatically. As shown in FIG. 11*a*, a user 1101 may position a simulated light source 1105 within a 3D data set 1130 within a plane 1120. In some embodiments, plane 1120 may correspond to an image plane of a 2D projection image. FIG. 11*a* shows a user positioning the simulated light source 1105 in the plane 1120 by placing a finger on a touch screen displaying a projected image rendered from the 3D data set 1130. However, other methods of positioning the light source 1105 may be used such as those discussed in reference to FIG. 7. A depth position of the light source 1105 within the 3D data set 1130 may be automatically determined based on a distance from a surface 1136 of a first region of interest 1135. The distance may be calculated according to one of or a combination of methods described above in reference to FIG. 10. When the user "drags" the light source 1105 to a new position in the plane 1120 and/or selects a new location in the plane 1120 on or near region of interest 1135, the light source 1105 may move along the path 1116, which defines a set distance from the surface 1136 of the region of interest 1135.

As shown in FIG. 11*b*, when the user positions the light source 1105 in the plane 1120 on or near a second region of interest 1137, the depth position of the light source 1105 may automatically adjust so that the light source 1105 is the same distance from a surface 1138 of the second region of interest 1137 that it was from the surface 1136 of the first region of interest 1135. In some embodiments, the set distance from the surface 1136 of the region of interest 1135 may be different from the set distance from the surface 1138 of the region of interest 1137. For example, if the distance between the simulated light source 1105 is determined based, at least in part, on a quality metric, the value of the quality metric calculated for region of interest 1135 may be different than the value of the quality metric calculated for region of interest 1137. When the user "drags" the light source 1105 to a new position in the plane 1120 and/or selects a new location in the plane 1120 on or near the region of interest 1137, the light source 1105 may move along the path 1117, which defines a set distance from the surface 1138 of the region of interest 1137. The technique 1000 illustrated in FIGS. 10 and 11*a-b* may allow a user to illuminate multiple areas of an image in succession without having to manually adjust the depth of the light source 1105. In some applications, this may save the user time as the user only has to choose an in-plane position for the light source 1105.

Features described with reference to image rendering technique 400 in FIG. 4 may be applied to the image rendering technique 1000 in FIGS. 10 and 11a-b. For example, the light source 1005, 1105 may be rendered in the image as an emissive object (e.g., glowing orb). The rendering of the light source 1005, 1105 in the image may be activated and/or deactivated automatically and/or by user selection. The light source 1005, 1105 may be rendered with a halo, which may be activated and/or deactivated automatically and/or by user selection. In some embodiments, a user may toggle between the image rendering technique 400 and image rendering technique 1000. For example, a clinician may survey a rendered image using image rendering technique 1000 and sweep the light source across several areas of interest in succession. When the clinician spots an area of particular interest (e.g., lesion), the clinician may switch to image rendering technique 400 to "fine tune" the position of the light source to examine the area in greater detail.

Figure 12:
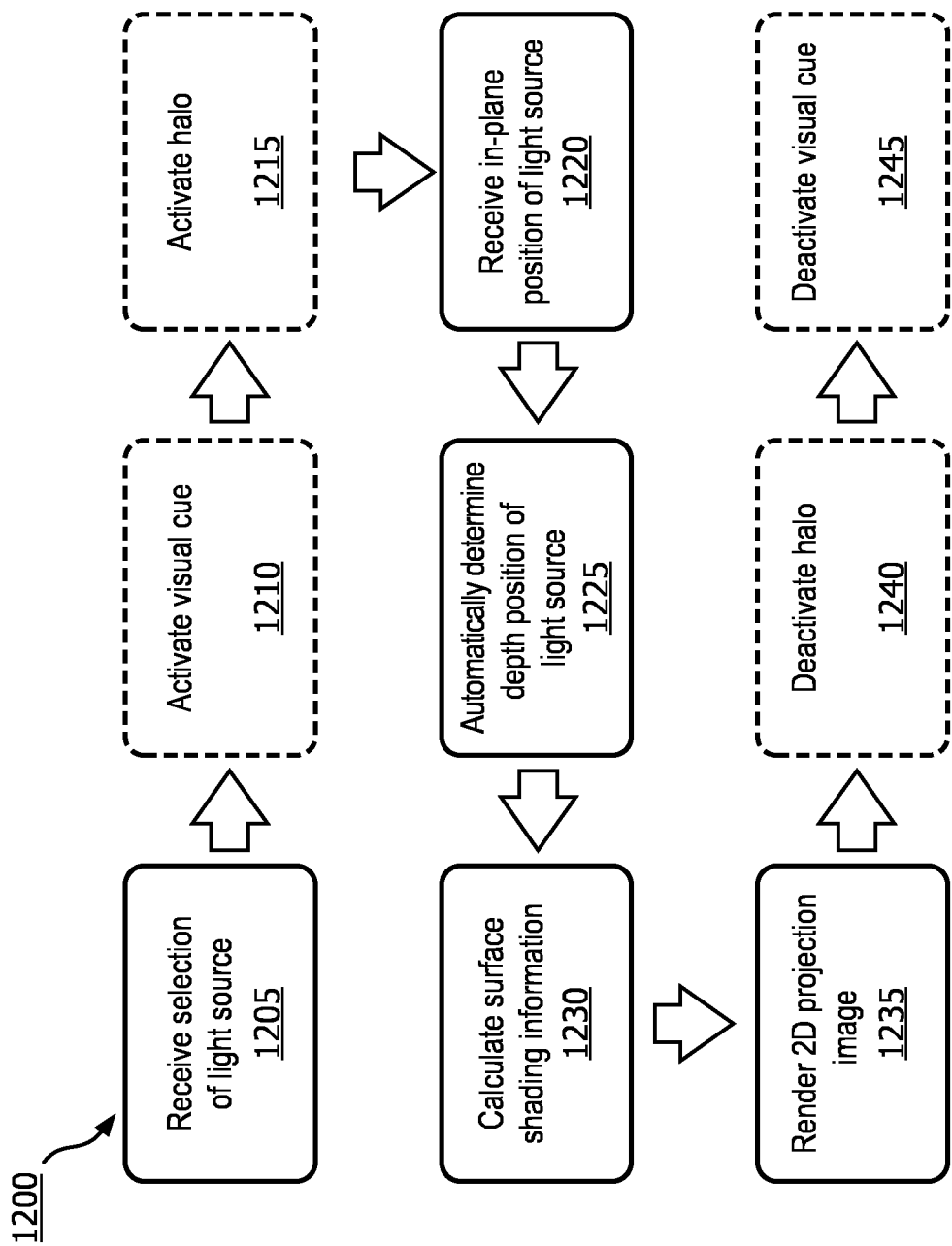
FIG. 12 is a flowchart of a method according to an embodiment of the disclosure.

FIG. 12 is a flowchart of a method 1200 for positioning a simulated light source within a 3D data set for rendering 2D projections from a perspective of a virtual observer of the 3D data set according to an embodiment of the disclosure. In some embodiments, method 1200 may be implemented using the image rendering technique 1000 illustrated in FIG. 10 and the ultrasound imaging system shown in FIG. 3. In some embodiments, a user may select a position of a simulated light source in a 3D data set prior to rendering of a 2D projection image of the 3D data set. In some embodiments, an imaging system may render a 2D projection image from a 3D data set with an initial default light source in a default position. The default light source and position may be pre-programmed into the imaging system and/or may be set by a user. In some embodiments, the default light source may be an external directional light source at fixed distance from the data set. In some embodiments, the default light source may be a multidirectional light source positioned within or near the 3D data set. At Step 1205, an imaging system may receive a selection of a simulated light source for rendering a 2D projection image of a 3D data set. In some embodiments, a user may select a simulated light source. The user may select the light source via a user interface such as user interface 24 in FIG. 1 or user interface 710 in FIG. 7. In some embodiments, the user may navigate through a user interface to enter a lighting control mode of the imaging system. In some embodiments, the user may tap a button or a touch screen to select the light source. Optionally, the user and/or imaging system may activate a visual cue of the light source at Step 1210. That is, the user may choose to have the light source rendered in the image as an object (e.g., an orb). In some embodiments, the light source may be rendered in the image by default. Optionally, the user and/or imaging system may activate a halo around the light source at Step 1215. In some embodiments, the light source may be rendered with a halo by default. In some embodiments, the user may prefer to render the image without the halo.

At Step 1220, the imaging system may receive an indication, responsive to user input, of an in-plane position of the simulated light source in a plane corresponding to a projection plane of the 2D projection image (e.g., image plane 1020 of FIG. 10). The user may select an in-plane position for the light source. The in-plane position may correspond to a position in the image plane in some embodiments. At Step 1225, a depth position of the simulated light source on an axis normal to the projection plane (e.g., Z-axis) may be automatically determined by the imaging system. In some embodiments, the depth position may be based on a set distance between the simulated light source and a surface in the region of interest. The depth position may correspond to the depth within the 3D data set in relation to the image plane. In some embodiments, Step 1225 and Step 1220 may be performed in reverse order. In some embodiments, Step 1220 and 1225 may be performed simultaneously. The user may select the in-plane position and depth position by using a track ball, a touch screen, and/or another method and/or user interface such as those described above in reference to FIG. 8. The imaging system may then calculate surface shading information for one or more surfaces in the 3D data set based on the in-plane and depth positions at Step 1230. At Step 1235, the imaging system may render the 2D projection image including the shading information on a display. In some embodiments, the imaging system may re-render the image as the in-plane position of the light source is moved by the user. That is, the light and shadows of the image may dynamically change as the position of the light source is altered (e.g., the depth position and surface shading information may be recalculated). This may allow the user to quickly compare potential positions of the light source and/or investigate features of the image by illuminating portions of the image in sequence. For example, the user may move the light source along a spinal column to examine each vertebra.

Once the light source is in position, the halo, if rendered, may be deactivated at Step 1240. In some embodiments, the user may choose to deactivate it (e.g., via a user interface). In some embodiments, the imaging system may automatically stop rendering the halo when the light source is stationary for a period of time. Alternatively, the halo may continue to be rendered. This may be desirable when the user has chosen a position for the light source that is outside the field of view. Optionally, at Step 1245, the visual cue for the light source may be deactivated. That is, the object rendered as the light source in the image may be removed from the image. The imaging system may deactivate the visual cue for the light source automatically or the user may choose to deactivate the visual cue for the light source. Deactivating the visual cue for the light source may be advantageous when the user wishes to observe minute features illuminated in the image near the light source.

Method 1200 may be performed during image acquisition in some embodiments. For example, the imaging system may render images from a 3D data set acquired from a matrix array ultrasound transducer during an ultrasound exam. Method 1200 may be performed on a 3D data set stored on an imaging system or other computing device (e.g., computer, hospital mainframe, cloud service). For example, a radiologist may review images rendered from a 3D data set acquired during a prior exam.

Although method 1200 is described with reference to a single light source, all or portions of method 1200 may be performed and/or repeated for multiple light sources. For example, a user may set a first light source at a first region of interest and a second light source at a second region of interest. This may allow the user to quickly highlight features of the 3D data set.

Figure 13A:
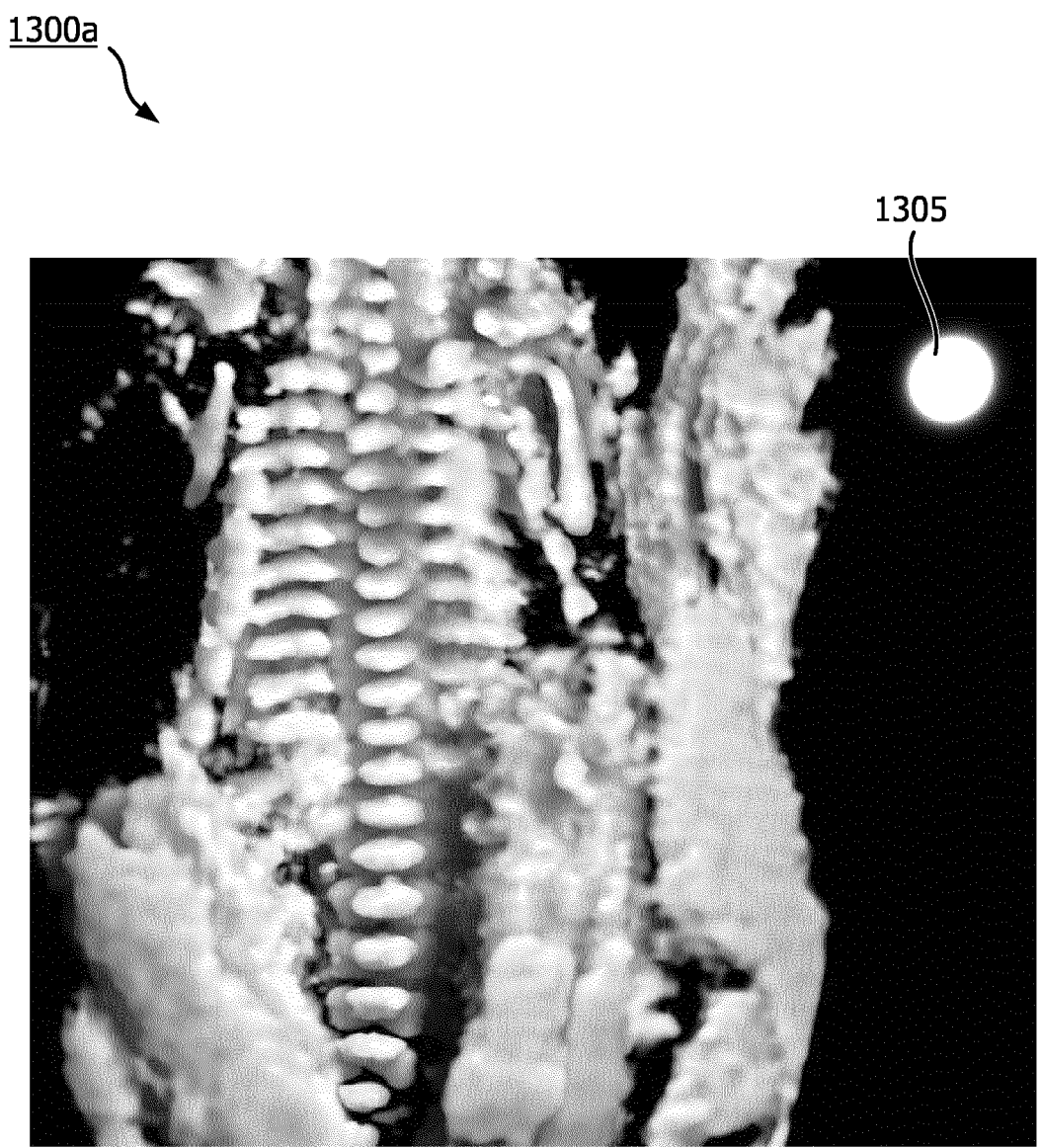
FIG. 13A-C are examples of rendered spinal column images according to an embodiment of the disclosure
Figure 13B:
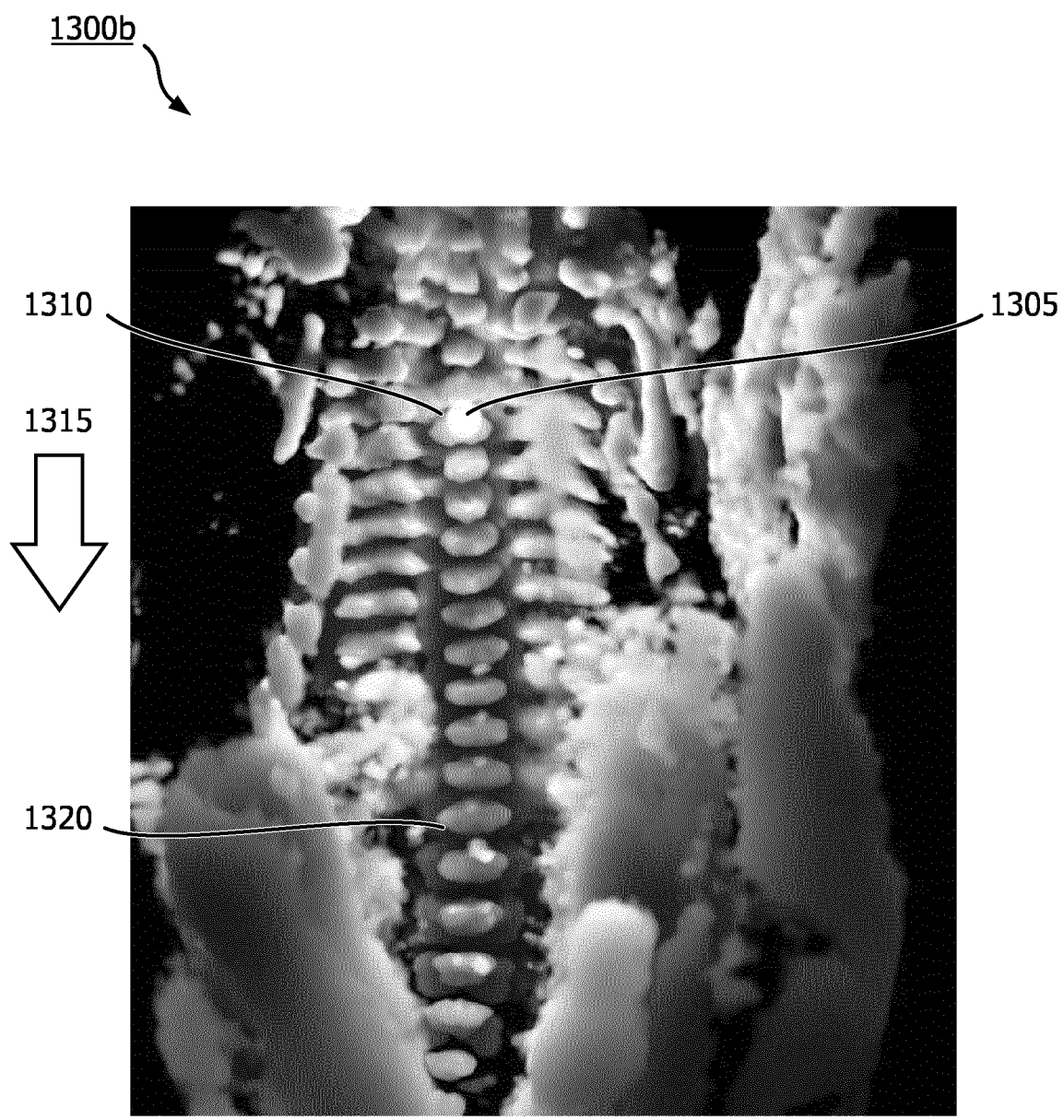
Figure 13C:
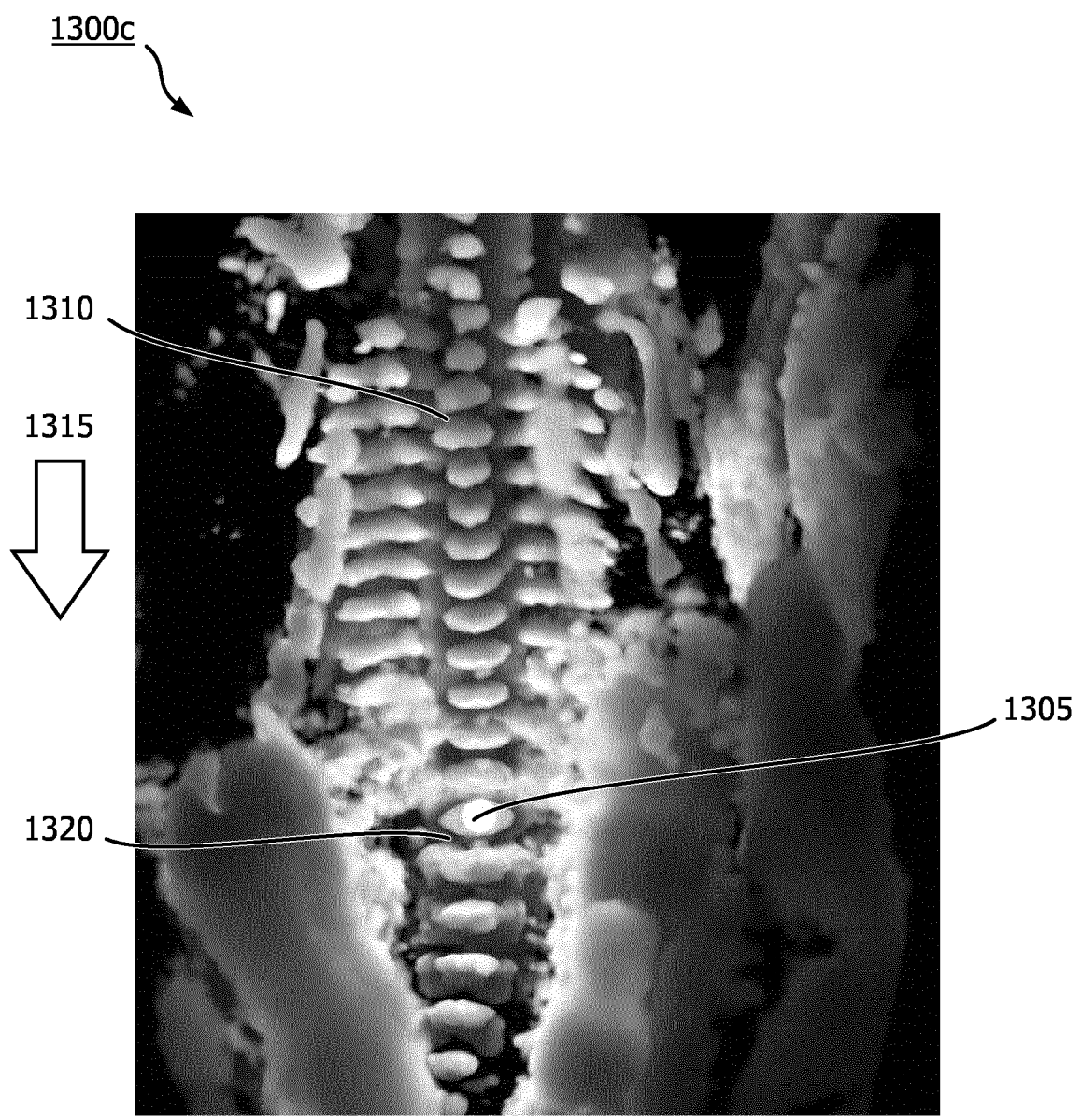

FIGS. 13a-c are examples of rendered spinal column images 1300a-c according to an embodiment of the disclosure. FIG. 13a shows spinal column image 1300a with a simulated light source 1305 rendered as a glowing orb. Spinal column image 1300a may have been rendered with the simulated light source 1305 in a default position. After spinal column image 1300a has been rendered, a user and/or an imaging system may adjust a position of the simulated light source 1305. FIG. 13b shows spinal column image 1300b with simulated light source 1305 over a vertebra 1310. The simulated light source 1305 may be a set distance from a surface of the vertebra 1310. The user may have adjusted the in-plane position of the simulated light source 1305 from the default position shown in image 1300a to the current position over the vertebra 1310 shown in image 1300b. The user may have adjusted the in-plane position of the simulated light source 1305 using one or more of the methods described previously in reference to FIG. 7. The imaging system may have automatically adjusted a depth position of the simulated light source 1305 such that the simulated light source 1305 is the set distance from the surface of the vertebra 1310. FIG. 13c shows spinal column image 1300c with simulated light source 1305 over a vertebra 1320. The simulated light source 1305 may be the set distance from a surface of the vertebra 1320. The user may have adjusted the in-plane position of the simulated light source 1305 from the position over vertebra 1310 shown in image 1300b to the current position over the vertebra 1320 shown in image 1300c. The user may have adjusted the in-plane position of the simulated light source 1305 using one or more of the methods described previously in reference to FIG. 7. For example, the user may have dragged the light source 1305 along a direction indicated by arrow 1315 using a touch screen. The imaging system may have automatically adjusted a depth position of the simulated light source 1305 such that the simulated light source 1305 is the set distance from the surface of the vertebra 1320. The imaging system may have automatically adjusted a depth position of the simulated light source 1305 as the user dragged the light source 1305 along the spinal column image 1300c between vertebra 1310 and vertebra 1320 such that the set distance between the light source 1305 and the surfaces shown in spinal image 1300c. The imaging system may have adjusted the depth position of light source 1305 using one or more techniques described in reference to FIGS. 10-12. This may allow a clinician to quickly scan the spinal column and inspect each vertebra.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. An ultrasound imaging system comprising:
a scan converter configured to generate a three dimensional data set from ultrasound echoes received from a subject when imaging a volume of the subject;
a volume renderer configured to calculate surface shading information of a first surface of the 3D data set based, at least in part, on a location of a simulated light source, wherein the location is within the 3D data set, and render a two dimensional projection image of the 3D data set which includes the shading information; and
a user interface comprising:
a display configured to display the 2D projection image; and
an input device comprising a user interface element configured to receive first user input indicative of an in-plane position of the simulated light source within a projection plane of the 2D projection image, wherein the volume renderer is further configured, responsive to movement of the simulated light source within the 3D data set via the user input, to automatically render the simulated light source at a location corresponding to the in-plane position and a depth position determined by the volume renderer, and wherein the depth position is set such that the simulated light source maintains a set distance from the first surface within the 3D data set as the simulated light source is moved over the first surface via the user input.

2. The imaging system of claim 1, wherein the depth position corresponds to a location along an axis normal to the projection plane at the set distance from the first surface of the 3D dataset, wherein the set distance is a constant distance from different positions on the first surface.

3. The imaging system of claim 2, wherein the set distance from the first surface of the 3D dataset is determined responsive to user input received prior to the first user input.

4. The imaging system of claim 2, wherein the set distance from the first surface of the 3D dataset is pre-programmed in memory of the ultrasound imaging system.

5. The imaging system of claim 1, wherein the user input element comprises a GUI displayed on a touchscreen of the ultrasound system, and wherein the GUI comprises a visual cue of the simulated light source displayed in the 2D projection image along with the rendered 3D dataset, and wherein the visual cue is movable, responsive to user input, to allow the user to dynamically change the in-plane position of the simulated light source in relation to the rendered 3D data set.

6. The imaging system of claim 5, wherein the visual cue includes an orb.

7. The imaging system of claim 6, herein the visual cue further includes a halo surrounding the orb.

8. The imaging system of claim 1, wherein the simulated light source is a multidirectional light source.

9. The imaging system of claim 1, wherein the first surface represents a boundary between two different materials of the imaged volume and wherein the set distance corresponds to a 1-10 millimeters offset from the boundary.

10. The imaging system of claim 1, wherein the volume renderer is further configured to position of the simulated light source at a second set distance from a second surface of the 3D dataset responsive to user input indicative of movement of the simulated light source to an in-plane position in front of the second surface, such that the simulated light source maintains the second set distance from the second surface as the simulated light source is moved over the second surface via the user input.

11. The imaging system of claim 1, comprising an ultrasound probe configured to receive the ultrasound echoes from the subject to image the volume of the subject.

12. The imaging system of claim 10, wherein the volume renderer is configured to dynamically adjust the depth position of the simulated light source when the in-plane position of the simulated light source is adjusted, based, at least in part, on whether the first surface or the second surface corresponds to the in-plane position of the simulated light source.

13. A method comprising:
receiving a selection of a simulated light source for rendering a 2D projection image of a 3D data set, wherein the 3D data set is constructed from ultrasound echoes received from a volume of a subject;
receiving an indication, responsive to user input, of an in-plane position of the simulated light source in a plane corresponding to a projection plane of the 2D projection image;
automatically determining a depth position of the simulated light source on an axis normal to the projection plane, wherein the depth position is set based on contours of the first surface, wherein a location of the simulated light source is within the 3D data set;
receiving indications, responsive to user inputs, of movement of the in-plane position of the simulated light source;
automatically adjusting the depth position to maintain a set distance between the simulated light source and the surface within the 3D data set as the in-plane position of the simulated light source is moved;
calculating surface shading information of a surface of the 3D data set based, at least in part, on the in-plane and depth positions; and
rendering the 2D projection image including the shading information on a display.

14. The method of claim 13, wherein the set distance is based, at least in part, on a distance at which a dynamic range of lighting intensity in the 2D projection image is maximized.

15. The method of claim 13, wherein the set distance is based, at least in part, on user input received via the user interface.

* * * * *